United States Patent [19]

Fox

[11] 4,443,242
[45] Apr. 17, 1984

[54] FOLIAR FEED

[75] Inventor: Rodney Fox, Cottingham, England

[73] Assignee: Reckitt & Colman Products Limited, United Kingdom

[21] Appl. No.: 340,462

[22] Filed: Jan. 18, 1982

[30] Foreign Application Priority Data

Jan. 21, 1981 [GB] United Kingdom ............... 8101804

[51] Int. Cl.³ .................................................. C05G 3/00
[52] U.S. Cl. ............................................ 71/11; 71/27; 71/28; 71/64.08; 71/64.1
[58] Field of Search ................. 242/305; 47/DIG. 11, 47/13; 71/64.08, 64.1, 11, 27, 28, 31

[56] References Cited

U.S. PATENT DOCUMENTS

| | | | |
|---|---|---|---|
| 3,089,280 | 5/1963 | Klaas | 47/DIG. 11 |
| 3,647,411 | 3/1972 | Stevens | 71/1 |
| 3,982,920 | 9/1976 | Cross et al. | 71/64.08 X |
| 4,002,456 | 1/1977 | Maas | 71/64.1 |
| 4,026,694 | 5/1977 | Cross et al. | 71/64.08 |
| 4,348,424 | 9/1982 | Consolazio et al. | 71/64.1 X |

OTHER PUBLICATIONS

Aerosols, Science & Technology, Shepherd, 1961, pp. 17-44 and 97.
The Science & Technology of Aerosol Packing, Sciarra et al., 1974, pp. 275-284.

Primary Examiner—Ferris H. Lander
Attorney, Agent, or Firm—Bacon & Thomas

[57] ABSTRACT

This invention relates to the foliar feeding of growing plants.

Conventional foliar feed comprising plant nutrients dissolved in water have a very poor shelf life and chemically attack many container materials. To overcome this problem the practice is to mix the aqueous solution feed immediately before use. In practice it is necessary to mix more solution than is required and, particularly with small scale applications, there is always a waste of feed.

The present invention overcomes this problem by providing an aerosol container charged with a foliar feed solution and a propellant, preferably forming a water in oil emulsion with the solution, and whereby the feed has a relatively long shelf life and can be dispensed in small quantities without wastage.

25 Claims, 1 Drawing Figure

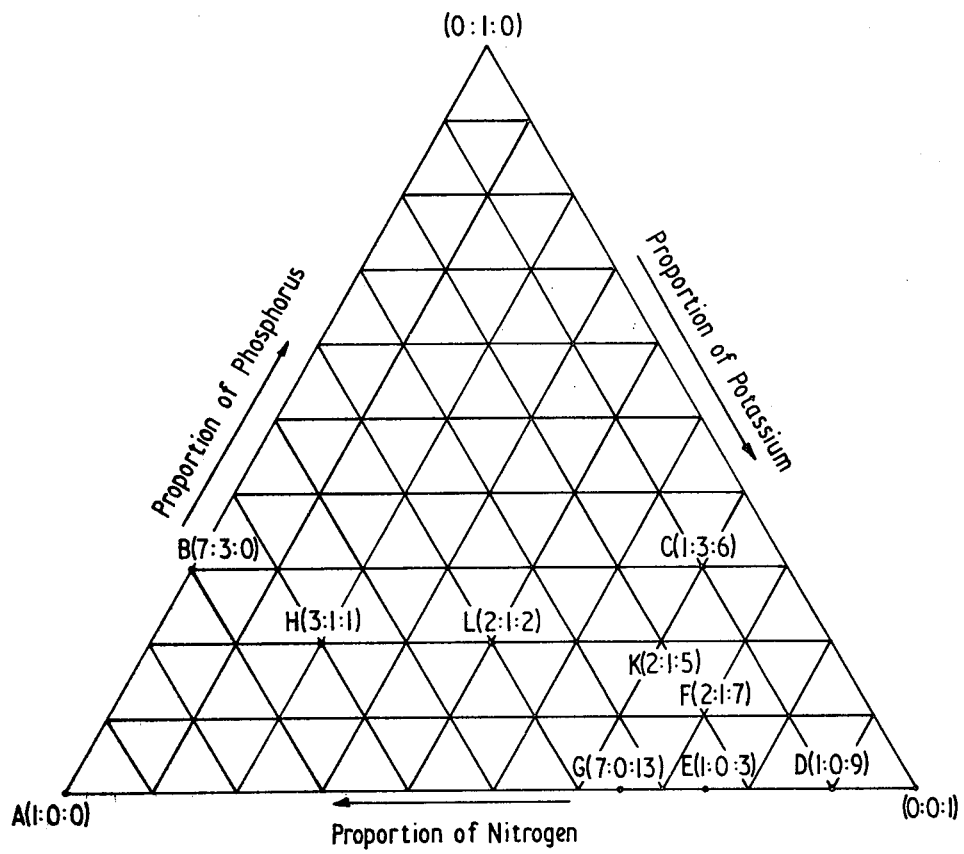

FOLIAR FEED

FIELD OF THE INVENTION

This invention relates to the foliar feeding of growing plants and more particularly to a method for the preparation of a foliar feed directly applicable to growing plants.

DESCRIPTION OF PRIOR ART

For proper growth plants need a supply of nutrients in addition to those synthesised and/or recycled by the subject plant. Such additional plant nutrients, including trace elements, are applied to the soil surface either in solid form for subsequent dissolution in water for absorption by the roots or are dissolved in aqueous medium for more immediate absorption through the roots. Alternatively, those plant nutrients, including trace elements, which are absorbable through the foliage of plants may be applied in aqueous solution directly to the foliage. Such latter method of application is known as foliar feeding, a method well known in agriculture and horticulture and of considerable value especially in the treatment of growing plants in a state of shock due to stress such as cold, drought, waterlogging of roots or overcrowding.

In conventional foliar feeding a suitable aqueous solution of plant nutrients is applied to the foliage as a spray from a dispensing container, for example, a water vessel fitted with a perforated nozzle to deliver water in fine jets or, alternatively, a so-called pump-pack which can dispense a spray under pressure of compressed air.

Suitable plant nutrient solutions for foliar feeding are freshly prepared as required from storage-stable solids compositions or from specially formulated storage-stable aqueous concentrates.

At the high dilutions required for direct application as foliar feed the balanced nature of foliar feed compositions may be disturbed on storage and can support unwanted bacterial growth; the dilute solutions tend to be sensitive to most metals that they contact, especially over protracted periods, and to avoid these problems the practice is to mix a desired solution immediately before use.

When a suitable dilute solution is to be batch mixed and charged to a dispensing container, preferably constructed from plastics material for immediate application to subject plants, it is usual for a relatively larger quantity of solution to be prepared than is required for actual foliar feeding because a minimum volume of liquid is required to ensure that the dispensing container operates properly, few people have the skill to judge the actual amount of solution necessary for a specific application and, as the instructions for mixing are generally given for specific batches, the correct mix can only be obtained by mixing a batch to the next highest order than that required. Therefore, after the correct application of solution to the subject plants, the balance is either poured away or it is applied to the soil, which latter step can result in over watering which can be deleterious to some plants.

It has been observed that in many cases house plants exist in a stressful environment, consequently failure of the plant may result from shock as in agriculture, or horticulture and foliar feeding is one useful means of counteracting the effects of shock.

Since for home use, on the relatively few plants that are kept in most domestic situations, only small quantities of the diluted plant nutrient solution are required at a given time it is wasteful and arguably ecologically hazardous to pour away unused excess of plant nutrients into a domestic drainage system.

A need arises, therefore, for a method of preparing plant nutrients, especially for foliar feeding on small scale usage for example in a domestic situation, in which the above disadvantages are removed or at least mitigated.

STATEMENT OF INVENTION

The present invention overcomes the prior art problems by providing a method for the preparation of a foliar feed composition comprising the steps of dissolving plant nutrient in water to form a foliarly effective aqueous solution thereof, charging the solution into a container, closable by a dispensing valve; and adding an aerosol propellant.

Thus, by the method proposed by the invention there is provided a ready to use foliar feed in aerosol form facilitating economic usage, particularly on small scale.

Preferably the method includes the steps of purging the head space of oxygen by displacement of air with aerosol propellant vapour by addition of boiling propellant either wholly or in part to the plant nutrients solution prior to closing the can. Alternatively, an inert gas may be employed as purger. Conveniently, a combination of these two may be employed optionally with the co-operative effect of a partial vacuum applied to the container; or a partial vacuum applied to the container alone may be employed.

Preferably, the composition includes a surfactant to produce an emulsion of the propellant oil phase and aqueous phases upon mixing the two.

Preferably, the emulsion is a so-called water-in-oil or oil-out emulsion in which the immiscible phases are the external phase which comprises the propellant and the aqueous phase is the internal phase.

The external phase is preferably extended with a propellant solvent, which is non-phytotoxic or of negligible phytotoxicity. The precise nature of the emulsion is determined by the relative phase volumes, chemical nature of the two phases and importantly the chemico-physical properties of the surfactant employed.

One preferred emulsion is a so-called quick breaking emulsion in which at least a part of the external oil phase separates out from the emulsion on standing to form a supernatant layer which layer on agitation, for example by shaking the container, is readily redispersed to a uniform emulsion in the container albeit temporarily, a quick breaking emulsion necessarily remains uniform for at least sufficient time after agitation for a dose of the product to be dispensed from the container.

For the preparation of such quick breaking emulsion a surfactant or surfactant blend which is an emulsifying agent providing an HLB number of from 3 to 6 is employed. HLB is an acronym for hydrophile lipophile balance in the well known "Atlas HLB System" which was designed to assist the production of satisfactory emulsions. Surfactants falling within this heading include the oleic and/or stearic acid esters of polyols, for example glyceryl monostearate; mixed stearate-oleates of glycerol ethoxylated derivatives thereof and mixtures of these classes.

In another aspect the present invention provides foliar feed compositions when produced by the method of the invention.

The plant nutrients are preferably water-soluble inorganic salts of certain metals such as potassium, magnesium and including trace elements, also ammonium salts to furnish the cations required and mixed to yield a variety of N:P:K ratios to suit a range of plants and conditions thereof as is already well known in agricultural and horticultural formulation. Further, the anions are preferably nitrates and phosphates in suitable cases. Urea which has been said to improve foliar feeding of plants when included in a foliar feed composition, may also be included. Other organic nitrogenous compounds may be used, such as soluble amino-acids, to achieve special effects on application to plants.

It may be desirable to include chelating agents to achieve solubility of some metals and trace elements, as is well known. Suitable chelating agents include for example ethylenediaminetetraacetic acid and its alkali metal salts.

It is important to avoid the use of over concentrated solutions for foliar feeding for such could cause scorching of the foliage, detrimental to the plant and at least unsightly on domestic foliage plants.

The present invention enables properly formulated, balanced foliar feeds to be provided without the user being concerned with the preparation of the feed and the user can simply spray the feed from the container.

Prior to charging a solution to the container the relative proportions of constituent plant nutrient salts can be varied to yield differing N:P:K values optionally with trace elements in particular products.

In the accompanying drawings the single FIGURE comprises a graph showing weight fractions 0 to 1 of phosphorous plotted against weight fractions 0 to 1 of potassium and 0 to 1 weight fractions of nitrogen for the purpose of illustrating N:P:K weight ratios useful for the practising of the present invention.

N:P:K ratios are herein expressed as weight proportions of the elements nitrogen, phosphorus and potassium. It is well known that the more important aspect of these ratios is the ratio N:K for phosphorus is principally used at the growing point of the plant and is translocated within the plant.

For foliar feeding, a dilute solution of pure urea has been found beneficial. Having regard to this, preferred compositions within the present invention will have N:P:K ratio within the area ABCD on the graph.

Plants in flower or in fruit need relatively more potassium than plants grown for their foliage which need relatively higher proportions of nitrogen.

More preferably the compositions within the present invention for use on foliage plants will have N:P:K ratio falling within the area defined by ABCG, preferably area AHKG. Conversely flowering plants will require compositions with N:P:K ratios preferably falling within the area defined by ALCD, more preferably area GLKFE.

The total level of plant nutrients is preferably less than 5% by weight of the aqueous phase to avoid scorching of plant leaves. The useful range probably lies between 0.01% and 5% by weight of the aqueous phase; preferably 0.05% to 0.5%. Typical commercially available trace elements preparations may be added at levels usually not exceeding 0.1% w/w of the aqueous phase.

Leaf shine agents to enhance the gloss of leaves may be included. Preferably, such materials are dissolved or dispersed in the oil phase. Suitable materials well known in the art include certain silicones, wax dispersions and non-drying vegetable oils.

The spray characteristics of the product of the present invention are characteristic of wet, surface sprays. In the case of a quick breaking emulsion the fineness of spray can be improved by use of a so-called vapour tap valve to close the container.

The invention is further illustrated by the following non-limitative Examples in which percentages are by weight of the final composition except where otherwise indicated.

EXAMPLE 1

A w/o emulsion was prepared from:

|  | % age |
|---|---|
| LIBFEED 3:1:1 | 1.019 |
| Deionised water | 55.080 |
| Butyl hydroxyanisole | 0.005 |
| Witconol 14 | 0.515 |
| ISOPAR G | 13.382 | and the liquid charged into lacquered aerosols cans, closed with a vapour tap valve and pressurised with butane to 40 psig. in the ratio emulsion: butane:; 70:30 by weight.

In glass containers the composition was seen to be an emulsion which sprayed a uniform spray on discharge. By holding the can approximately 30 cm away from the leaves being sprayed no thermal shock was experienced by the plant.

EXAMPLE 2

An aqueous solution of plant nutrients was prepared containing:

|  | % age |
|---|---|
| Ammonium dihydrogen phosphate | 0.18 |
| Potassium nitrate | 0.27 |
| Magnesium sulphate (dried) | 0.004 |
| Urea | 0.560 |
| Librate A-Z (Chelate Mix) | 0.002 |
| Water | 55.08 |

This solution was emulsified with ISOPAR G (13.382%) containing butylhydroxyanisole (0.005%) using Witconol 14 (0.515%) as emulsifier to produce a w/o emulsion.

70 parts of the emulsion pressurised with 30 parts butane (40 psig) was filled into internally lacquered aerosol cans fitted with a vapour tap valve.

The emulsion product was found to be adequately stable on storage; partial separation of the emulsion did occur but complete emulsification followed shaking prior to dispensing. No valve blockage due to deposition of crystals was observed.

The compositions of the Examples when properly sprayed onto plants foliage produce no chilling thereof that could lead to shock in the plants. Further, no separation of the water-borne components from solution occurred when spray droplets arrived at the foliage.

It is believed that by slightly spacing the aerosol dispenser from the foliage e.g. 30 cm from the foliage the propellants components are evaporated—producing a chilling effect—to reduce spray particle size as dispersed and the spray particles become reheated to at least near room temperature by further passage through the air before alighting on the foliage. Foliar feeding demands that the nutrients be in solution on the foliage. Solids deposits per se are not absorbed through foliage.

Various aqueous solutions containing the concentrations of the salts, to yield the approximate N:P:K ratios, shown in Table 1 were prepared.

Aliquots of each solution, to provide a final concentration of 2.5% w/w total salts, were charged into internally lacquered aerosol cans to leave a head space.

The head space was purged of oxygen by displacement of the air by means of a partial vacuum applied to the mouth of the can.

The can was then charged with butane aerosol propellant in the weight ratio 45:55:butane:solution and closed with a vapour tap valve.

By vigorous shaking of the can immediately prior to discharge, a wet relatively coarse spray was produced on discharging a sample. By judicious choice of valve the spray may be produced as fine as desired.

The sprays were applied to the foliage only of both monocotyledonous plants and dicotyledonous plants kept in the laboratory in plant pots. The plants included the following:- ivy (Hedera); ferns:- sword fern (Nephrolepis) and maidenhair fern (Aiantum); rubber tree plant (Ficus), Swiss cheese plant (Monstera), pelargoniums, Philodendrons, Mother-in-Law's tongue (Sansevieria), Impatients, Pointsettia (Euphorbia) and Chlorophytum.

No scorching was observed to develop and the treated plants thrived.

TABLE 1

| Example No. | Ammonium Nitrate % age w/w | Mono ammonium Phosphate % age w/w | Diammonium Phosphate % age w/w | Potassium Nitrate % age w/w | Urea % age w/w | Calculated N:P:K ratios |
|---|---|---|---|---|---|---|
| 3 | 60 | — | 15 | — | 25 | 10:1:0 |
| 4 | 50 | — | 20 | — | 30 | 8:1:0 |
| 5 | 60 | — | 25 | — | 15 | 6:1:0 |
| 6 | 30 | — | 40 | — | 30 | 10:3:0 |
| 7 | 60 | — | 25 | 15 | — | 5:1:1 |
| 8 | 60 | 25 | — | 15 | — | 27:7:6 |
| 9 | 60 | — | 15 | 25 | — | 8:1:3 |
| 10 | 60 | 15 | — | 25 | — | 13:2:5 |
| 11 | 50 | — | 20 | 30 | — | 11:2:5 |
| 12 | 30 | 40 | — | 30 | — | 2:1:1 |
| 13 | 50 | 20 | — | 30 | — | 26:6:13 |
| 14 | 30 | — | 40 | 30 | — | 8:3:4 |
| 15 | 15 | 15 | 15 | 40 | 15 | 3:1:2 |
| 16 | — | 20 | — | 60 | 20 | 4:1:4 |
| 17 | 10 | 10 | 10 | 60 | 10 | 4:1:5 |
| 18 | 5 | 5 | 5 | 80 | 5 | 7:1:12 |
| 19 | — | 10 | — | 80 | 10 | 6:1:12 |
| 20 | — | 10 | — | 70 | 20 | 8:1:10 |
| 21 | 5 | 10 | 5 | 70 | 10 | 5:1:7 |
| 22 | — | 20 | — | 70 | 10 | 3:1:5 |
| 23 | — | 25 | — | 75 | — | 2:1:4 |
| 24 | — | — | — | — | 100 | 1:0:0 |

I claim:

1. A method for the preparation of a foliar feed comprising the steps of:
   (a) dissolving plant nutrient in water to form a foliarly effective aqueous solution thereof;
   (b) forming a water-in-oil emulsion by mixing the said foliarly effective aqueous solution and an aerosol propellant in the presence of a surfactant providing an HLB in the range of from 3 to 6;
   (c) containing the said water-in-oil emulsion in an aerosol container; and,
   (d) purging oxygen from the container.

2. A method as claimed in claim 1 including the step of adding aerosol propellant to the emulsion-charged container.

3. A method for the preparation of a foliar feed as claimed in claim 1 including the step of adding an oil of negligible phytotoxicity to extend the oil phase of the emulsion.

4. A method for the preparation of a foliar feed as claimed in claim 1, comprising the steps of
   (a) charging the said foliarly effective aqueous solution into the said container,
   (b) adding the aerosol propellant to the said container; and
   (c) emulsifying the said foliarly effective aqueous solution and the said aerosol propellant in said container in the presence of a surfacent providing an HLB in the range of from 3 to 6.

5. A method as claimed in claim 1 including the step of agitating the said container to obtain or complete the emulsification of the container contents.

6. A method as claimed in claim 1 including the steps of mixing an oil of negligible phototoxicity with the aqueous solution in the presence of the surfactant to form an emulsion thereof prior to charging into the container.

7. A method of foliar feeding growing plants comprising the steps of:
   (a) dissolving plant nutrient in water to form a foliarly effective aqueous solution thereof;
   (b) forming a water-in-oil emulsion by mixing the said foliarly effective aqueous solution and an aerosol propellant in the presence of a surfactant providing an HLB in the range of from 3 to 6;
   (c) containing the said water-in-oil emulsion in an aerosol container;
   (d) purging oxygen from the container;
   (e) agitating the can-contents to homogenize the contents; and,
   (f) discharging a dose of can-contents in spray form onto growing foliage.

8. A method of foliar feeding growing plants as claimed in claim 7 comprising the steps of (a) charging the said foliarly effective aqueous solution into said container;
(b) adding said aerosol propellant to the container; and
(c) emulsifying the said foliarly effective aqueous solution and the said aerosol propellant in said container.

9. A method as claimed in claim 7 including the setp of adding an oil of negligible phytotoxicity.

10. A ready to use foliar feed composition comprising an aqueous phase containing dissolved plant nutrient and an oil phase including an aerosol propellant and a surfactant providing an HLB in the range of from 3 to 6 enclosed in a hand-operable pressure dispensing container, said plant nutrient comprising a soluble blend of salts containing potassium, phosphorous and nitrogen, and wherein the N:P:K ratio lies in the ratio range defined by the area ABCD on the accompanying graph.

11. A ready to use foliar feed composition as claimed in claim 10 in which the N:P:K ratio lies in the ratio range defined by the area ABCG on the accompanying graph.

12. A ready to use foliar feed composition as claimed in claim 10 in which the N:P:K ratio lies in the ratio range defined by the area AHKG on the accompanying graph.

13. A ready to use foliar feed composition as claimed in claim 10 in which the N:P:K ratio lies in the ratio range defined by the area ALCD on the accompanying graph.

14. A ready to use foliar feed composition as claimed in claim 10 in which the N:P:K ratio lies in the ratio range defined by the area GLKFE on the accompanying graph.

15. A ready to use foliar composition comprising a water-in-oil emulsion, the aqueous phase containing dissolved plant nutrient and the oil phase including an aerosol propellant and a surfactant providing an HLB in the range of from 3 to 6 the emulsion being contained in a hand-operable pressure dispensing container.

16. A ready to use foliar feed composition as claimed in claim 15 wherein the plant nutrient includes organic nitrogen-containing materials.

17. A ready to use foliar feed composition as claimed in claim 15 wherein the plant nutrient comprises a soluble blend of salts containing potassium, phosphorus, nitrogen, magnesium and trace elements.

18. A ready to use foliar feed composition as claimed in claim 15 wherein the plant nutrient includes urea.

19. A ready to use foliar feed composition as claimed in claim 15 in which the surfactant is present in an amount of from 0.1% to 5% by weight of the total composition.

20. A ready to use foliar feed composition as claimed in claim 15 including an oil of negligible phytotoxicity.

21. A ready to use foliar feed as claimed in claim 20 in which the oil is iso-dodecane or a petroleum fraction with low aromatics content.

22. A ready to use foliar feed composition as claimed in claim 15 in which the oil phase comprises from 45% to 70% by weight of the total composition.

23. A ready to use foliar feed as claimed in claim 15 and wherein the aerosol propellant is a hydrocarbon, a hologenated hydrocarbon or a blend thereof.

24. A ready to use foliar feed as claimed in claim 15 and wherein the aerosol propellant is present in an amount of from 35% to 45% by weight of the total composition.

25. A ready to use plant nutrient composition as claimed in claim 15 and wherein the plant nutrient comprises 0.01% to 5% by weight of the aqueous phase.

* * * * *